United States Patent
Chang et al.

(10) Patent No.: US 9,740,824 B2
(45) Date of Patent: Aug. 22, 2017

(54) DRINKING WATER REMINDING SYSTEM AND REMINDING METHOD THEREOF

(71) Applicant: TAIWAN GOMET TECHNOLOGY CO., LTD, New Taipei (TW)

(72) Inventors: Sheng-Hsiung Chang, New Taipei (TW); Sheng-Yuan Chang, New Taipei (TW)

(73) Assignee: Taiwan Gomet Technology Co., Ltd., New Taipei (TW)

( * ) Notice: Subject to any disclaimer, the term of this patent is extended or adjusted under 35 U.S.C. 154(b) by 561 days.

(21) Appl. No.: 13/839,690

(22) Filed: Mar. 15, 2013

(65) Prior Publication Data

US 2014/0046596 A1 Feb. 13, 2014

Related U.S. Application Data

(60) Provisional application No. 61/680,722, filed on Aug. 8, 2012.

(51) Int. Cl.
*G01F 1/00* (2006.01)
*G06F 19/00* (2011.01)

(52) U.S. Cl.
CPC ...... *G06F 19/3406* (2013.01); *G06F 19/3475* (2013.01)

(58) Field of Classification Search
CPC .......... G06F 19/3406; G06F 19/3475
USPC ...................................... 702/3, 45
See application file for complete search history.

(56) References Cited

U.S. PATENT DOCUMENTS

| | | | | |
|---|---|---|---|---|
| 2006/0064037 A1* | 3/2006 | Shalon | ............... | A61B 5/0006 600/586 |
| 2006/0278156 A1* | 12/2006 | Miller | ............... | A47G 23/14 116/112 |
| 2007/0222619 A1* | 9/2007 | Moran | ............... | G01F 1/075 340/573.1 |
| 2011/0149693 A1 | 6/2011 | Liao | | |
| 2011/0263946 A1* | 10/2011 | el Kaliouby | ............... | A61B 5/1128 600/300 |
| 2013/0095459 A1* | 4/2013 | Tran | ............... | A61B 5/6816 434/247 |

FOREIGN PATENT DOCUMENTS

| | | |
|---|---|---|
| CN | 201312699 Y | 9/2009 |
| JP | 3771911 | 5/2006 |
| JP | 2006251871 A | 9/2006 |
| JP | 2009034223 A | 2/2009 |

(Continued)

*Primary Examiner* — Stephanie Bloss
(74) *Attorney, Agent, or Firm* — Muncy, Geissler, Olds & Lowe, P.C.

(57) ABSTRACT

Disclosed is a drinking water reminding system and the reminding method thereof. The water intake of user is measured by the operation of a reminder of the drinking water reminding system, and a collector of the drinking water reminding system is provided for adjusting the daily drinking water demand of user according to environmental parameters or the physiological parameters of user. The drinking water reminding system reminds the user to drink water if the drinking water reminding system determines that the user has taken insufficient water according to predetermined conditions and measurement results, drinking water reminding system.

25 Claims, 17 Drawing Sheets

(56) References Cited

FOREIGN PATENT DOCUMENTS

| JP | 2009245171 | A | 10/2009 |
|---|---|---|---|
| TW | M369446 | U1 | 11/2009 |
| WO | WO2012098602 | A1 | 7/2012 |

* cited by examiner

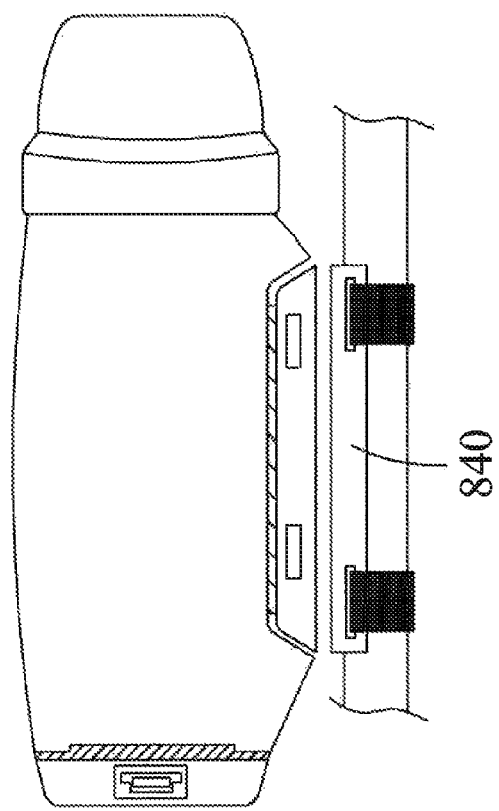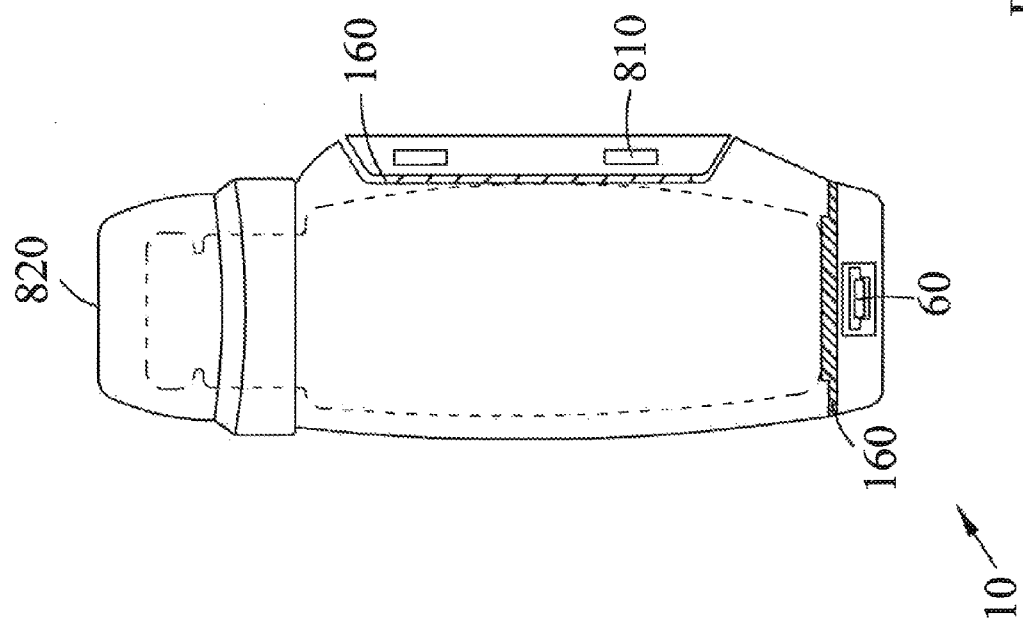
FIG. 8

DRINKING WATER REMINDING SYSTEM AND REMINDING METHOD THEREOF

CROSS-REFERENCE TO RELATED APPLICATION

This application claims the benefit of U.S. provisional application No. 61/680,722 filed on Aug. 8, 2012, in the United States Patent and Trademark Office, the disclosure of which is incorporated herein in its entirety by reference.

FIELD OF THE INVENTION

The present invention relates to a reminding system and its reminding method, and more specifically to the drinking water reminding system and method that remind users about the updated drinking water information by means of a pair of reminder and collector connected with one other.

BACKGROUND OF THE INVENTION

According to the general standard of daily water intake recommended by medical professionals, most people do not drink enough water and are usually situated in a slightly dehydrated status due to abnormal living habits, busy works or reluctance of drinking water, and thus resulting in discomforts including stomachache, headache and back pain. In a more serious situation, drinking insufficient water may cause health problems such as causing kidney stones. Particularly for patients who have taken kidney stone surgery, more water than ordinary people should be taken in order to wash away or discharge the crushed stones out of the patients' body. However, most patients suffer with kidney stone generally do not have the habit of drinking sufficient water, and they may forget to drink more water after taking the surgical operation. As a result, kidney stones recur habitually.

At present, most drinking water reminders available in the market are used to determine whether or not sufficient water is taken by counting the number of cups of water being taken per day or reading the scales marked on a container. However, patients still may forget that the number of cups of water has been taken or take a wrong reading from the calibration.

Therefore, it is necessary to provide a drinking water reminding system for measuring the amount of water taken every day automatically in different occasions of our daily activities and taking the statistics of the required water intake and water supplement correctly, while updating the cumulative water intake and taking the statistics by a cloud server simultaneously.

SUMMARY OF THE INVENTION

In view of the problems of the prior art, it is a primary objective of the present invention to provide a drinking water reminding system to overcome the problems of the conventional reminder incapable of counting a water intake of user, since the user may easily forget counting the number of cups of water intake or take a wrong reading. The drinking water reminding system of the invention comprises at least one reminder and at least one collector, wherein the at least one reminder is connected and paired with the at least one collector. The reminder further comprises a measuring module, an input and a display interface, a first processing module, a first storage module, a first reminding module and a first transmission module. Wherein, the measuring module is arranged for measuring the content in the container to obtain a measurement signal; the input and display interface is provided for inputting a user data of the user including age, sex, weight, working mode or daily starting/ending time of drinking water; the first processing module is provided for calculating a total personal daily drinking water demand and an average predetermined water intake at different time intervals according to the input data and arranged for receiving the measurement signal, and calculating the measurement signal to obtain at least one measurement result; the first storage module is arranged for storing the measurement result and the predetermined water intake; the first reminding module is arranged for performing a reminding action according to the predetermined condition and the measurement result; and the first transmission module is arranged for transmitting the measurement signal and the drinking water record to a personal electronic storage device such as a computer or a mobile device via a cable or wireless transmission mode and transmitting the drinking water record and data to a cloud server via network or telecommunication.

Preferably, the drinking water reminding system further comprises a server. After the reminder and the server are connected, the server synchronously receives the personal measurement record and creates a personal drinking water record, and further creates a personal drinking water reference table by a plurality of user data. Wherein, the server calculates a drinking water demand curve for a particular day according to the user data including physiological data such as sex, age, body weight, type of work and daily drinking water time and meteorological parameters including the weather, temperature, humidity, ultraviolet or duration of sunshine of the place where the user is located, or other parameters and data. The drinking water demand curve is set as a basis for the drinking water standard of the reminder or the collector to replace the original average predetermined water intake calculated by the reminder to remind the user to drink different amount of water intakes at different time periods. In the meantime, the server analyzes the actual drinking water records from different users and provides the statistics and analyzed drinking water records to other users with similar backgrounds for reference to adjust the drinking water program.

Preferably, the collector further comprises a sensing module, a second processing module, a second storage module, a second reminding module and a second transmission module. Wherein, the sensing module is arranged for obtaining an environmental parameter and a physiological parameter; the second processing module is arranged for receiving a measurement signal, calculating the measurement signal to obtain a measurement result, and adjusting a predetermined condition according to the environmental parameter or the physiological parameter; the second storage module is arranged for storing the measurement result and the predetermined condition; the second reminding module is arranged for performing a reminding action according to the predetermined condition and the measurement result; and the second transmission module is arranged for transmitting the measurement signal and the predetermined condition between the reminder and the collector in a wireless transmission mode. When the reminder or the collector establishes connection and pairing with each other, the reminder, the collector or combination thereof performs a reminding action.

Preferably, when the paired reminder and collector are unable to establish a connection, the first reminding module and the second reminding module perform the reminding action according to the predetermined condition and the measurement results stored in the first storage module and the second storage module respectively. When the paired reminder and collector cannot establish an connection, the collector issues an offline warning to notice a user that the reminder and the collector are unable to be connected, while the collector further provides a user input interface for the user to input the amount of water intake by the user during the period when the reminder and the collector cannot establish the connection. Finally, when any one of the reminder and the collector have been reconnected and paired, the measurement signal, the measurement result and the amount of water intake are synchronously updated to the reminder and the collector.

Preferably, the reminder and the collector further comprise an interface conversion device connected to an electronic device via a cable or wireless connection for transmitting the reminding action, the personal drinking water record or the personal drinking water reference table to the electronic device.

Preferably, the measurement method includes a weight measurement method, an optical measurement method, an ultrasonic measurement method or an electrical impedance variation measurement method.

Preferably, the reminding module includes a light emitting unit, a sound unit and/or a vibrating unit.

Preferably, the predetermined condition includes a water intake within a predetermined time or a water intake set by the user.

Preferably, the sensing module includes a global positioning system, a multi-axis accelerometer, an electronic compass, a gyroscope, a hygrometer or various different physiological signal sensors.

Preferably, the environmental parameter includes temperature, humidity and ultraviolet of the location of user and the moving speed, acceleration or direction of the user Preferably, the physiological parameter includes pulse, body temperature, sweat salinity or amount of exercise of the user.

Preferably, the reminder can be connected to the container by an attaching component corresponding to an attaching pad and an attaching layer. The attaching component comprises a magnet, a Velcro's tape, a latching element or a locking element, and the attaching pad is made of metal, plastic or ceramic, and the attaching layer can be an adhesive layer with a frictional layered structure.

Preferably, the reminder can be connected to the container by a fastener having screw threads or serration.

Another objective of the present invention is to provide a drinking water reminding method applied to a drinking water reminding system, and the method comprises the steps of performing the measurement method by the measuring module of the reminder to obtain the measurement signal, sensing the environmental parameter and the physiological parameter by the sensing module of the collector, establishing a connection between the first transmission module of the reminder and the second transmission module of the collector through the wireless transmission mode to transmit the measurement signal, the environmental parameter, the physiological parameter, the predetermined condition or combination thereof, calculating the measurement signal to obtain the measurement result by the first processing module or the second processing module and adjusting the predetermined condition according to the environmental parameter and the physiological parameter, and storing the measurement result and the predetermined condition in the first storage module and the second storage module and performing the reminding action according to the predetermined condition and the measurement result by the first reminding module, the second reminding module or combination thereof.

Preferably, the reminder and/or the collector can use the obtained environmental parameter and physiological parameter to calculate the adjusted predetermined condition, and synchronously update and distribute the adjusted predetermined condition to the connected reminder and/or collector.

Preferably, the reminder and/or the collector can use the obtained measurement signal to calculate a measurement result and then update and distribute the measurement result to the connected reminder and/or collector.

Preferably, the drinking water reminding method further comprises the step of performing the reminding action by the first reminding module and the second reminding module according to the predetermined condition and the measurement results stored in the first storage module and the second storage module respectively when the reminder and collector designed to be paired are unable to connect with each other, and synchronously updating and integrating the measurement result and the predetermined condition stored in the first storage module and the second storage module respectively before the reconnection when the reminder and collector are reconnected. Furthermore, the collector issues an offline warning to notice the user that the reminder and the collector designed to be paired are unable to connect with each other when the reminder and the collector are unable to establish the connection. Also, the collector provides a user input interface for the user to input the amount of water intake of the user during the period when the reminder and the collector are unable to establish the connection. Until any one of the reminder and the collector reconnects and gets paired, the measurement signal, the measurement result and the amount of water intake are updated synchronously to the reminder and the collector.

Preferably, the drinking water reminding method further comprises the step of synchronously receiving the measurement result and the predetermined condition to create a personal drinking water record after the reminder or the collector establishes a connection with a server, and using a plurality of user data to create a personal drinking water reference table by the server. Wherein, the server stores the measurement result, the predetermined condition or the personal drinking water reference table of different users in order to provide the reference of daily water drinking adjustment to different users.

Preferably, when the reminder or the collector is connected to the server or electronic device being connected to the server, the environmental parameter or the physiological parameter is uploaded into the server for personal record, at the same time the server download the user location weather forecast parameter (meteorological parameters) to the reminder or the collector, so the personal drinking water reference table stored in the reminder or the collector could be updated immediately by the environmental parameter, the physiological parameter and weather forecast parameter (meteorological parameters).

In summation of the description above, the drinking water reminding system and the reminding method thereof in accordance with the present invention have one or more of the following advantages:

(1) The drinking water reminding system and the reminding method thereof of the present invention calculates the cumulative water consumption by subtracting the weight of water and a container after drinking from the total weight of water and the a container before drinking or by a difference of the volume of water, so that users can use their own preferred container to calculate the drinking water consumption without inputting the net weight volume of the container in advance.

(2) The drinking water reminding system and the reminding method thereof of the present invention allow users to set their own drinking goal. Through a cloud database, the aforementioned results would be considered as a reference to plan a progressive drinking program of the user, and the progressive drinking program can be adjusted according to the body weight change of the user every day. The drinking water record of the user can further be reviewed or provided for personal or medical reference.

BRIEF DESCRIPTION OF THE DRAWINGS

FIG. 8 is a schematic view of a drinking water reminding system and the reminding method thereof in accordance with a fourth preferred embodiment of the present invention;

DESCRIPTION OF THE PREFERRED EMBODIMENTS

The technical characteristics, contents, advantages and effects of the present invention will be apparent with the detailed description of a preferred embodiment accompanied with related drawings as follows. It is noteworthy that same numerals are used to represent respective elements in the following preferred embodiments.

Figure 1:
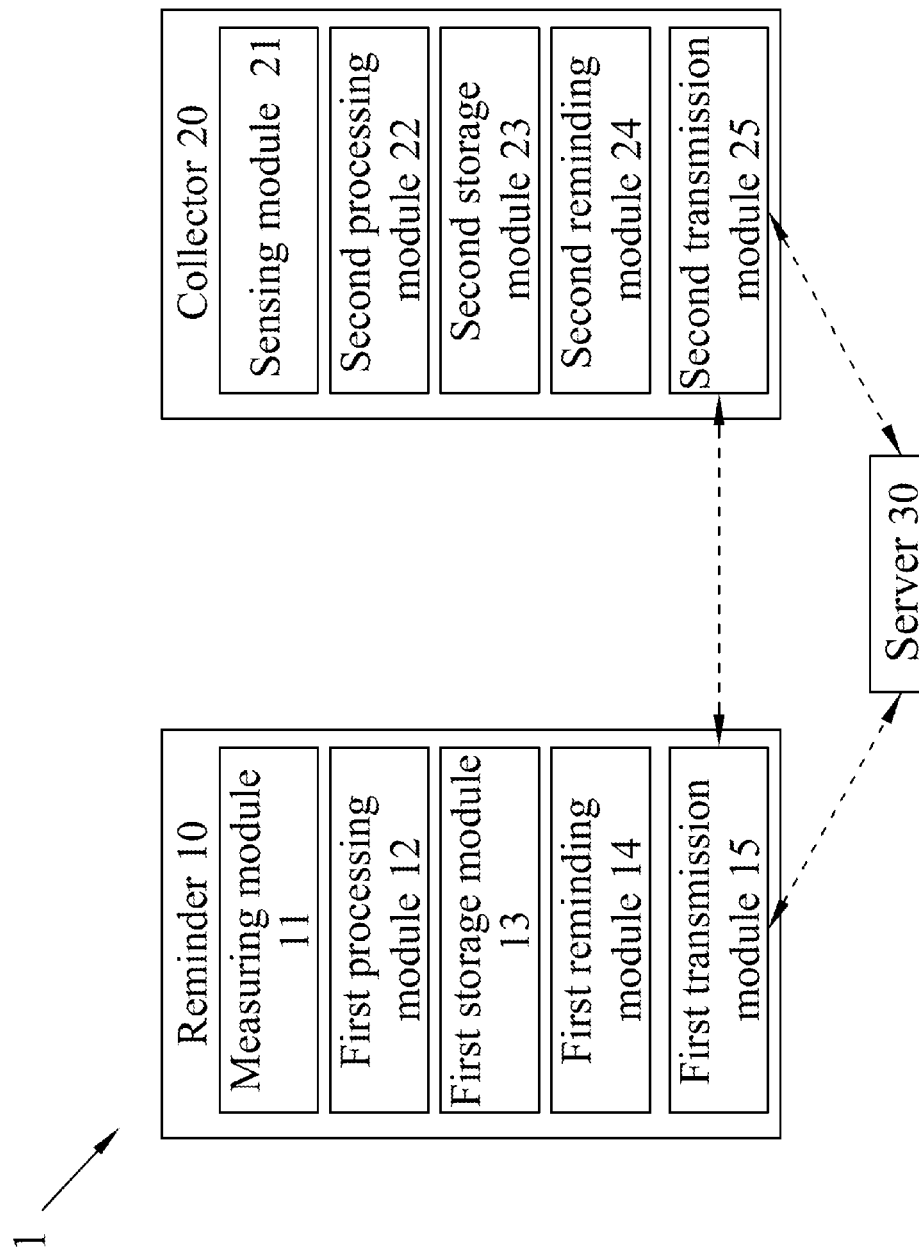
FIG. 1 is a first schematic view of a drinking water reminding system and the reminding method thereof of the present invention.

With reference to FIG. 1 for a first schematic view of a drinking water reminding system of the present invention, the drinking water reminding system 1 comprises at least one reminder 10 and at least one collector 20. The reminder 10 comprises a measuring module 11, a first processing module 12, a first storage module 13, a first reminding module 14 and a first transmission module 15. Wherein, the measuring module 11 is arranged for measuring a content in a container to obtain at least one measurement signal by using at least one measurement method; the first processing module 12 is arranged for receiving the measurement signal, and calculating the measurement signal to obtain a measurement result; the first storage module 13 is arranged for storing the measurement result and a predetermined condition; the first reminding module 14 is arranged for performing a reminding action according to the predetermined condition and the measurement result; and the first transmission module 15 is arranged for transmitting the measurement signal through a wireless transmission.

In addition, the collector 20 comprises a sensing module 21, a second processing module 22, a second storage module 23, a second reminding module 24 and a second transmission module 25. Wherein, the sensing module 21 is arranged for sensing a environmental parameter and a physiological parameter; the second processing module 22 is arranged for receiving measurement signal and calculating the measurement signal to obtain a measurement result, and adjusting a predetermined condition according to the environmental parameter and the physiological parameter; the second storage module 23 is arranged for storing the measurement result and the predetermined condition; the second reminding module 24 is arranged for performing a reminding action according to the predetermined condition and the measurement result; and the second transmission module 25 is arranged for transmitting the measurement signal and the predetermined condition between the reminder 10 and the collector 20 through the wireless transmission mode. Wherein, when the reminder 10 or the collector 20 establishes a connection and pairing, the reminder 10 and/or the collector 20 performs a reminding action.

Wherein, the measurement method includes a weight measurement method, an optical measurement method, an ultrasonic measurement method or an electrical impedance variation measurement method. The first reminding module 14 and the second reminding module 24 include a light emitting unit, a sound unit and/or a vibrating unit. The predetermined condition includes a weight variation within a predetermined time or a drinking water weight set by a user, or a measurement signal obtained by the aforementioned different measurement methods and its variation, and these predetermined conditions are used together with the measurement results obtained from different measurement methods to perform a reminding action. The sensing module includes a global positioning system, a multi-axis accelerometer, an electronic compass, a gyroscope, a hygrometer or a physiological signal sensor used for sensing the obtained environmental parameter and physiological parameter. Wherein, the environmental parameter includes temperature, humidity or ultraviolet of a location wherein a user is situated, or the user's moving speed, acceleration or direction; and the physiological parameter includes a user's pulse, body temperature or sweat salinity.

It is noteworthy that when the paired reminder 10 and collector 20 cannot establish a connection within a valid connection range, the first reminding module 14 and the second reminding module 24 perform a reminding action according to the predetermined condition and the measurement results stored in the first storage module 13 and the second storage module 23 respectively. In addition, while the reminder 10 and the collector 20 are unable to establish a connection, the collector 20 issues an offline warning to notice the user that the reminder 10 and the collector 20 are out of connection. Besides, the collector further provides a user input interface for the user to input the amount of water intake or the count of mouthful drinking water during the period when the reminder 10 and the collector 20 are offline. When the reminder 10 and the collector 20 are reconnected or returns to the valid connection distance range, the measurement signal, the measurement result and the amount of water intake are synchronously updated to the reminder 10 and the collector 20, so as to keep the data stored in the two device are the same, and to enhance the accuracy of measuring the water intake.

In addition, the drinking water reminding system 1 further comprises a server 30. When the reminder 10 and/or the collector 20 are connected to and paired with the server 30, the server 30 synchronously receives the measurement result and the predetermined condition to further create a personal drinking water record. Further, a personal drinking water reference table is created by using a plurality of user data inputted by the user during the connection of the server 30 and the reminder 10 and/or the collector 20. In other words, the user can obtain the drinking water record anytime and anywhere through the connection to the server, and the user can have more understanding on the drinking habit of their own. The personal drinking water reference table can also be used as a reference value for other users to adjust their drinking water program. Preferably, the server further collects and analyzes the measurement results, the predetermined conditions or the personal drinking water reference tables of different users by various different methods to provide them as reference for different users and to adjust the drinking water program. For example, the predetermined condition includes a user's height, weight, age, or sex and weather change, humidity change, duration of sunlight or intensity of ultraviolet in different areas where the user is situated. Therefore, users requiring to work with intensive physical strength or sit in an office for a long time can use the drinking water reminding system 1 of the present invention to take the aforementioned variable conditions into consideration to obtain the total water intake demand and the drinking water requirement curve at different time periods more accurately and to provide these information as a reference of drinking water for the users.

Figure 2:
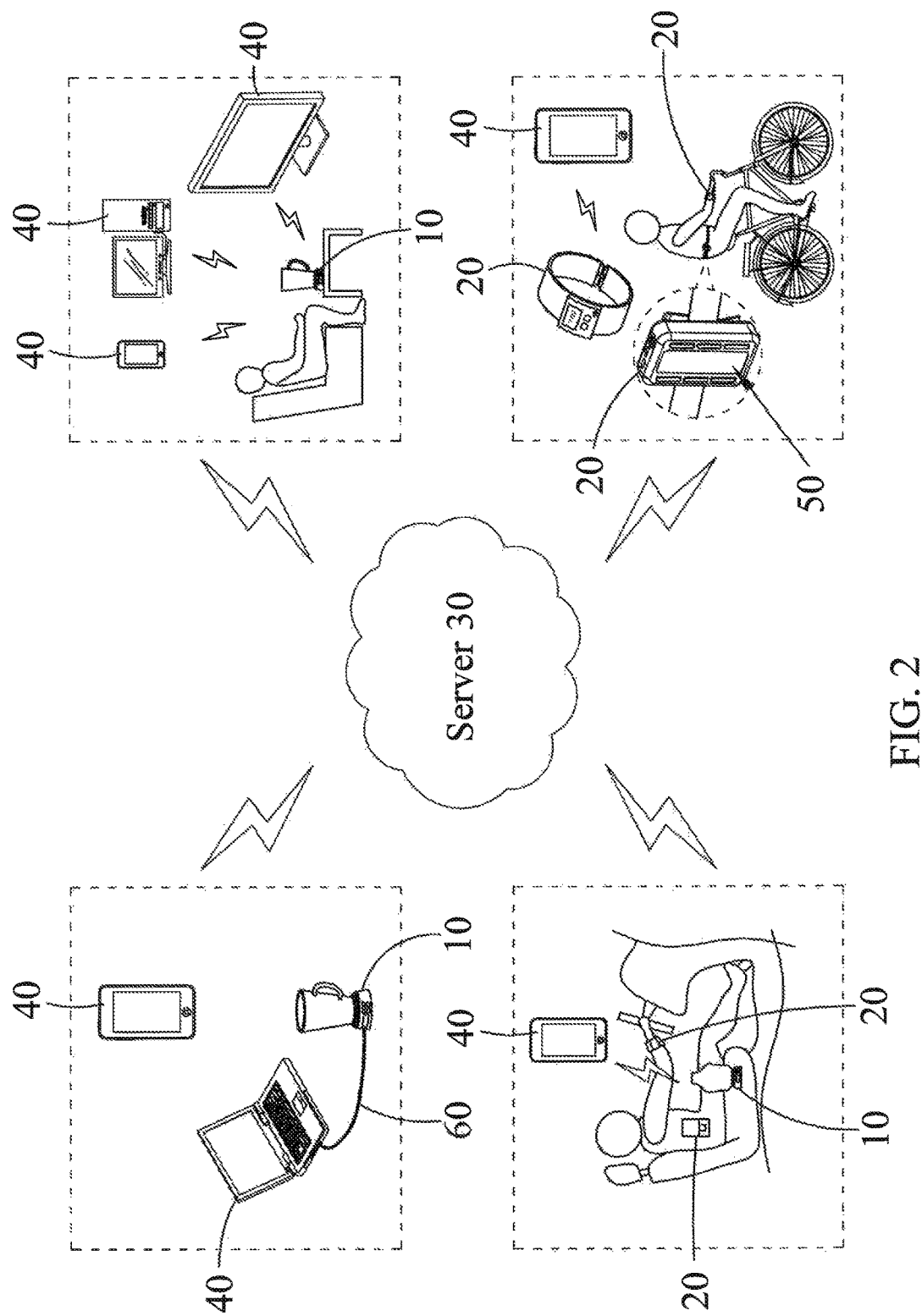
FIG. 2 is a second schematic view of a drinking water reminding system and the reminding method thereof of the present invention.

With reference to FIG. 2 for the second schematic view of a drinking water reminding system in accordance with the present invention, the drinking water reminding system 1 can be applied in daily life including but not limited to its application in an office or a dinning room or while driving or exercising. It is noteworthy that the reminder 10 and the collector 20 further include an interface conversion device 60 connected to an electronic device 40 via a cable or wireless connection for transmitting a reminding action, a personal drinking water record or a personal drinking water reference table to the electronic device 40. If the reminder 10 and/or the collector 20 is connected and paired with the server 30 via network, the measurement signal, the measurement result and/or the predetermined condition can be timely updated to the server 30. In other words, the drinking water reminding system provides a drinking water reference or a drinking water reminder to users in daily life and works with various different electronic devices 40 to provide the aforementioned information to users anytime and anywhere. The invention not only improves the convenience of use, but also lets the users build up a good habit of drinking water at regular time. In other words, the drinking water reminding system 1 of the present invention can monitor and urge the users to maintain the good habit of drinking sufficient water everyday by the electronic devices 10 having vibrations, sounds, images, tactile alert, auditory alert or visual alert produced by the users' peripherals such as a handheld device, a computer or a television screen via a cable or wireless transmission, even when the users are at a place away from the reminder 10. When the collector 20 carried by the users are offline or not paired, the users still can use the input interface 50 of the collector 20 to input the amount of water taken, and then synchronously update this information for the next time when the collector 20 is reconnected with any paired reminder 10 and adjust the predetermined condition in order to provide a drinking water reminder more accurately. Therefore, users can avoid symptoms caused by insufficient water intake and bringing uncomfortable physical mechanisms to the users by reminding the users to drink sufficient water. The drinking water reminding system of the present invention further can overcome the problems of the conventional drinking water reminding methods that the users may take a wrong reading of the scales of the container or forget counting the number of cups of water has been taken, or miscount the number of cups of water. In addition, the reminding system of the present invention further comprises a mute design, a visual and vibration effect and a pause reminding function that provides variety choices to users to prevent the users from being interfered in some occasions, such as in a meeting or conference.

Further, the first reminding module 14 and the second reminding module 24 of the reminder 10 and the collector 20 can use different colors of lights to represent the level of water intake. For example, white color stands for excessive drinking of water, and a progressive change of colors from a light yellow color to a yellowish orange color and finally to a red color represents various a decreasing level of water deficiency respectively, and such color change represents a change of colors of the urine of the user and the obvious color change can remind the users about the required amount of water intake.

Figure 3:
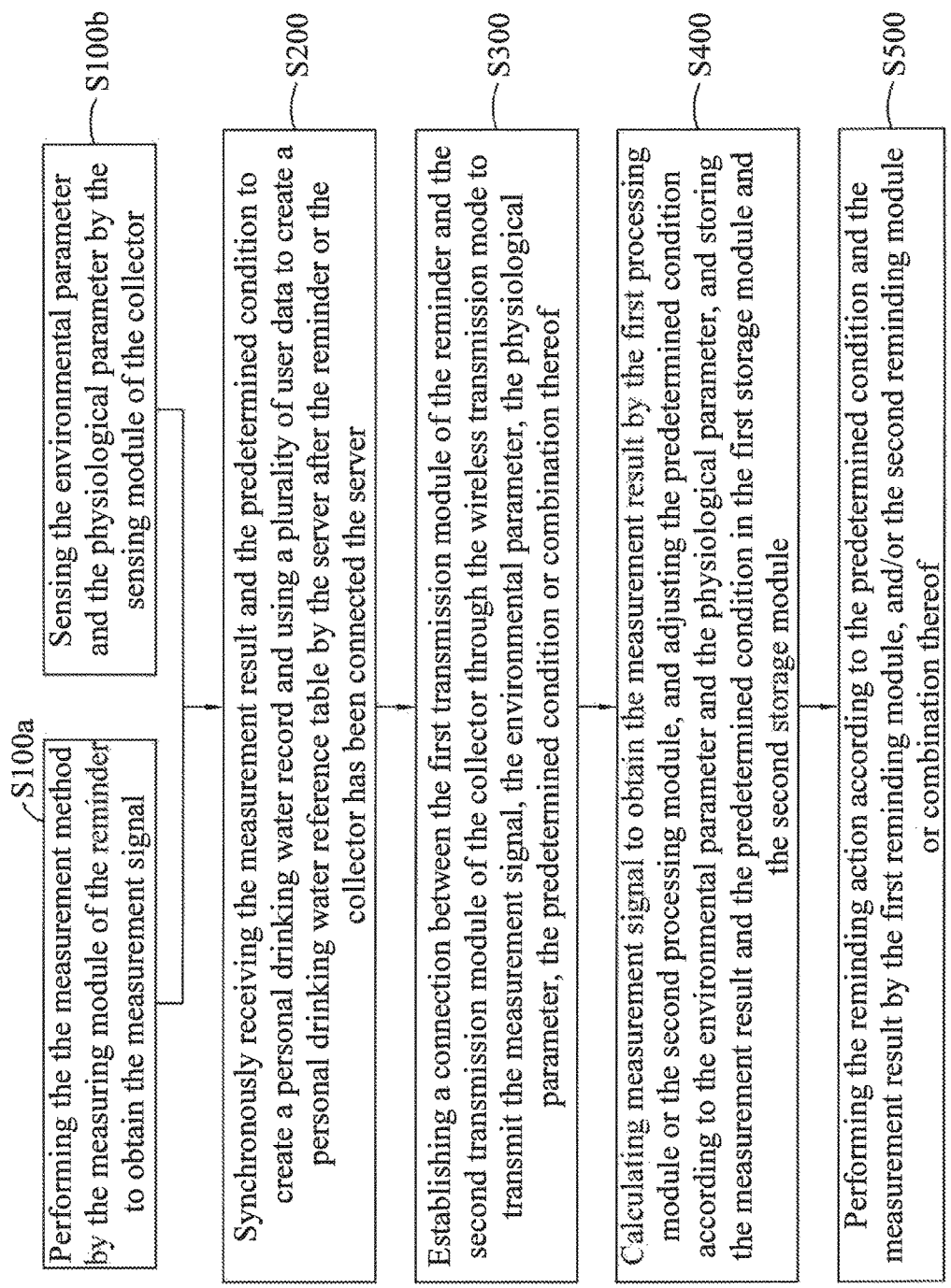
FIG. 3 is a flow chart of a drinking water reminding method of the present invention.

With reference to FIG. 3 for a flow chart of a drinking water reminding method of the present invention, the method comprises the following steps:

S100a: Performing the measurement method by the measuring module of the reminder to obtain the measurement signal.

S100b: Sensing the environmental parameter and the physiological parameter by the sensing module of the collector.

S200: Synchronously receiving the measurement result and the predetermined condition to create a personal drinking water record and using a plurality of user data to create a personal drinking water reference table by the server after the reminder or the collector has been connected the server.

S300: Establishing a connection between the first transmission module of the reminder and the second transmission module of the collector through the wireless transmission mode to transmit the measurement signal, the environmental parameter, the physiological parameter, the predetermined condition or combination thereof.

S400: Calculating measurement signal to obtain the measurement result by the first processing module or the second processing module, and adjusting the predetermined condition according to the environmental parameter and the physiological parameter, and storing the measurement result and the predetermined condition in the first storage module and the second storage module.

S500: Performing the reminding action according to the predetermined condition and the measurement result by the first reminding module, and/or the second reminding module or combination thereof.

In addition, the obtained environmental parameter and physiological parameter can be used by the reminder 10 and/or the collector 20 to compute the adjusted predetermined condition, and then synchronously update the adjusted predetermined condition to the paired reminder 10 and/or collector 20 via a connection, so as to reduce the waste of electric power caused by computing the predetermined condition repeatedly.

In addition, the obtained measurement signal can be used by the reminder 10 and/or the collector 20 to compute a measurement result first and then synchronously update the measurement result to the connected reminder 10 and/or collector 20 via a connection, so as to reduce the waste of electric power caused by computing the predetermined condition repeatedly.

In addition, the reminder 10 can notice an application program of electronic device or mobile device of other persons to assist monitoring and reminding the user to drink water, to take medicine or food intake and so on through network software application or a wireless connection signal while performing the reminding action.

It is noteworthy that the method further comprises the following steps. When the paired reminder 10 and collector 20 cannot establish a connection, the first reminding module 14 and the second reminding module 24 perform the reminding action according to the predetermined condition and the measurement results stored in the first storage module 13 and the second storage module 23 respectively. The collector 20 issues an offline warning to notice a user that the reminder 10 and the collector 20 cannot be connected, while the collector 20 further provides a user input interface 50 to input the amount of water taken by the user during the period when the reminder 10 and the collector 20 cannot establish the connection. Until the reminder 10 and the collector 20 re-establish a connection and pairing, the measurement signal, the measurement result and the amount of water taken are synchronously updated to the reminder 10 and the collector 20 to obtain a more accurate drinking water reminder.

Preferably, the method further comprises the following steps. After the reminder 10 or the collector 20 is connected with the server 30, the server 30 receives the measurement result and the predetermined condition synchronously and creates a personal drinking water record, and then uses a plurality of data inputted by the user during the connection and pairing processes to create a personal drinking water reference table. Wherein, the server 30 stores the measurement results, predetermined conditions or personal drinking water reference tables of different users and provides these data to different users for their reference and making adjustments to their drinking water program or goal.

Furthermore, when the reminder 10 or the collector 20 is connected to the server 30 directly or via the electronic device 40 being connected to the server 30, the environmental parameter or the physiological parameter is uploaded into the server 30 for personal record, at the same time the server 30 download the user location weather forecast parameter (meteorological parameters) to the reminder 10 or the collector 20, so the personal drinking water reference table stored in the reminder 10 or the collector 20 could be updated immediately by the environmental parameter and the physiological parameter and weather forecast parameter (meteorological parameters).

With reference to FIGS. 4 to 17 for preferred embodiments of the present invention respectively, it is noteworthy that same numerals are used for representing same respective elements of the embodiments respectively.

A user can configure settings for connecting and pairing a reminder 10 and/or a collector 20 with a server 30 as follows:

Configuration Method 1: The user can input her/his body weight and current work or rest conditions (such as working in office, doing a physical work or exercising, having or not having air condition, and available drinking time) through the drinking water reminding system 1. For example, the user can drink water during office hour or anytime other than sleeping, so that the drinking water reminding system 1 of the present invention can calculate the user's drinking water requirement per day or a period of time.

Configuration Method 2: The user can input her/his name, race, sex, age, diseases in her/his living area in addition to the aforementioned data through an electronic device 40 such as a computer or a handheld device, and then connect the network through the server 30 to add the regional weather data, variables and conditions such as temperature, humidity, sunshine and ultraviolet intensity and duration into the calculation to obtain a more accurate total drinking water requirement and date of a drinking water requirement curve at different time.

Configuration Method 3: The user can input his desired daily water intake (or mediation) directly.

Configuration Method 4: The server 30 collects the drinking water records of other users and analyzing and classifying the drinking water records to provide statistics of users of different backgrounds and average water intake as a reference value such as the ethnic origin, the weather required in a district, the type of work or age, and the reference value is divided by the user's drinking time in a daily rest and work schedule to calculate the user's personal average water intake per unit time, and finally, the calculated result is transmitted to the drinking water reminding system 1 to complete the configuration.

Figure 4:
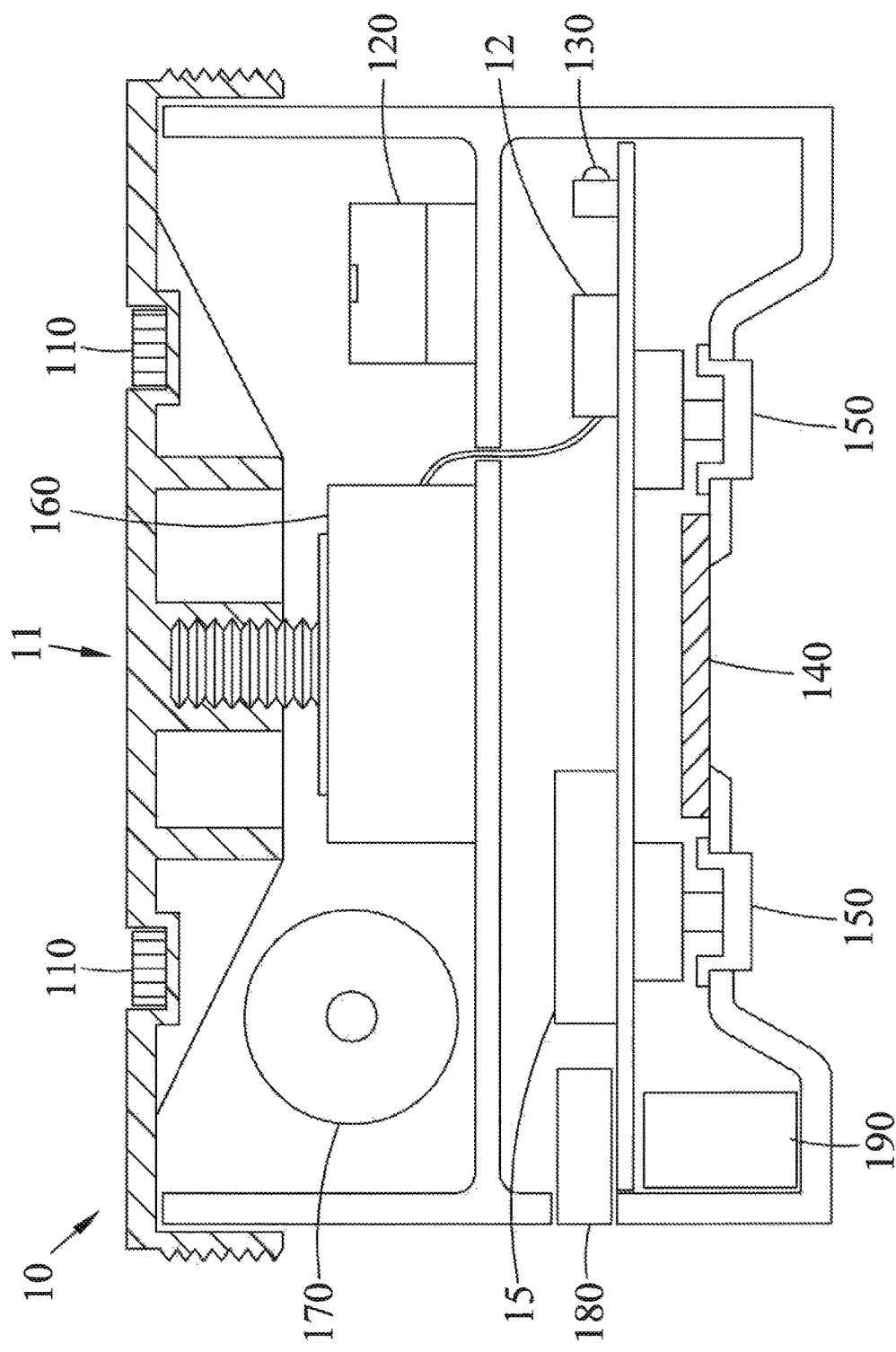
FIG. 4 is a schematic view of a drinking water reminding system and the reminding method thereof in accordance with a first preferred embodiment of the present invention.

When the user put a water glass filled with water or any appropriate container on the measuring module 11 of the reminder 10 of the drinking water reminding system 1 of the present invention (as shown in FIG. 4) driven by a power supply 17, the load cell sensor 160 in the measuring module 11 senses a weight variation, and then the first processing module 12 starts executing the timing and counting processes automatically after a buffer time for avoiding accidental touches passes, so as to obtain a measurement signal. Wherein, the measuring module 11 further comprises an adhesive element 110 for attaching various additional attachments of different shapes thereon, so that diversified containers can be mounted onto the measuring module 11. When the predetermined inspection time is up, the measurement result produced by the measurement signal remains unchanged. When the variation of the measurement result satisfies the predetermined condition, it means that the user has forgotten drinking water or refilling water in the cup as required. Therefore, the first reminding module 14 performs a reminding action by issuing a long or short beep and sounds with different intervals according to the level of required supplement of water (such as the buzzer 120 as shown in FIG. 4 or any other similar sound generating devices), making a change of colors of a light (such as the LED 130 as shown in FIG. 4), producing different frequencies or vibrations of different cycles (such as the driving motor 190 as shown in FIG. 4) to actively remind the user to supplement water again at this stage. The reminder 10 of the present invention also connects to an application program (APP) of an electronic device or a mobile device by the first transmission module 15 via a cable or wireless connection to automatically show a video on a display screen or produce a vibration to remind the remaining amount of water required to be supplemented at the stage. Until the reminder 10 determines that the user has drunk water exceeding a cumulative water consumption of the predetermined condition or the user has pressed a press button 150 or a touch screen 140 to input a specific signal before stopping the alarm.

In addition, the daily drinking water records stored in the first storage module 13 are outputted from the interface conversion device 60 to a personal storage device or a server 30 via a cable (such as I/O Port, USB, and LAN) or the first transmission module 15 via a wireless signal (such as Wi-Fi, Bluetooth, zigbee, Ant, RF and IR) at a fixed time or anytime. The user can connect an application program (APP) of a handheld device such as a mobile phone, a Pad, a notebook (NB), a computer or a Smart TV online with a server 30 to obtain a water supplement warning and a drinking water requirement or record information, and observe and analyze one's drinking water data hourly/daily/monthly or within any time period.

Figure 5:
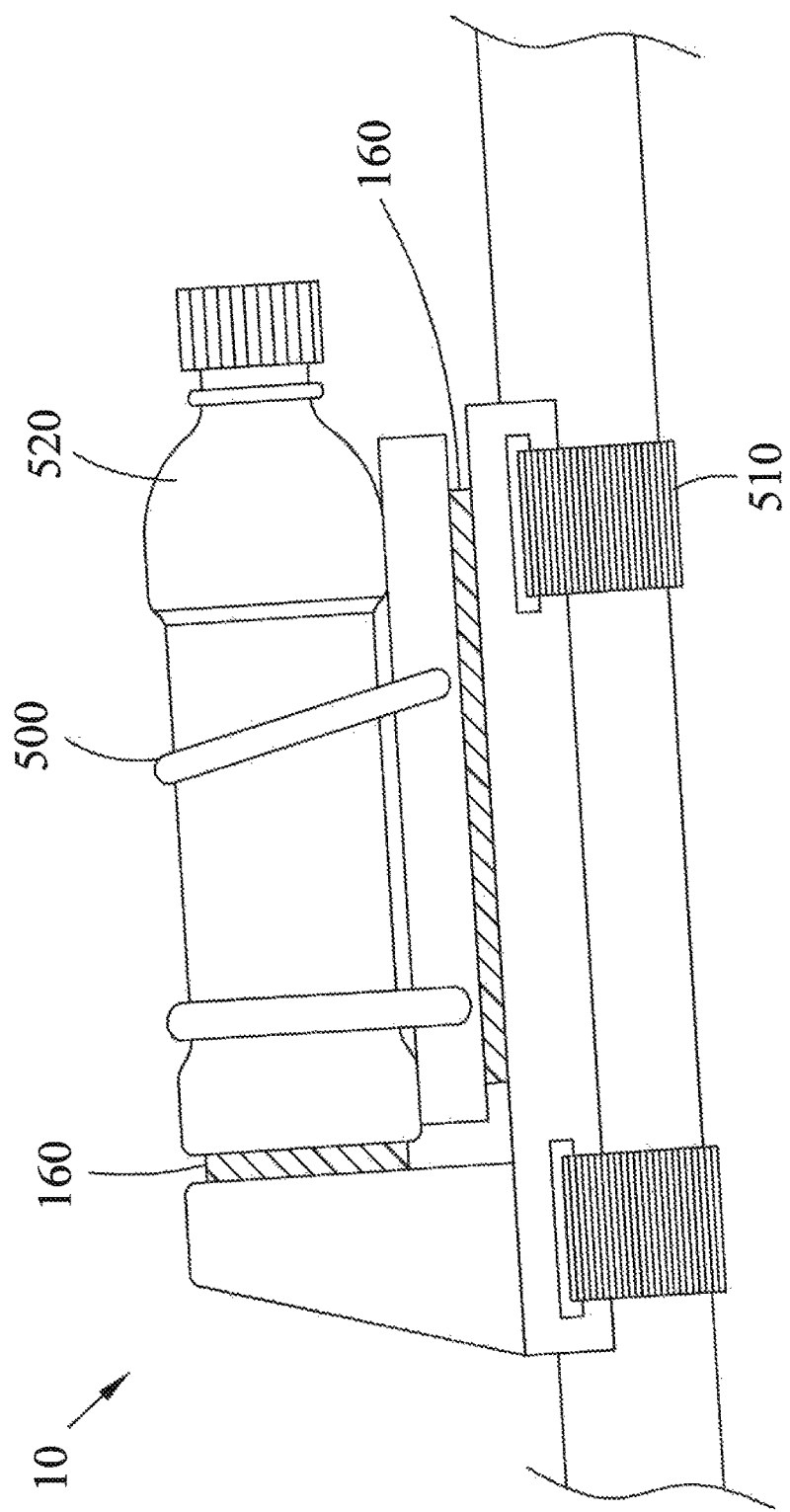
FIG. 5 is a first schematic view of a drinking water reminding system and the reminding method thereof in accordance with a second preferred embodiment of the present invention.
Figure 6:
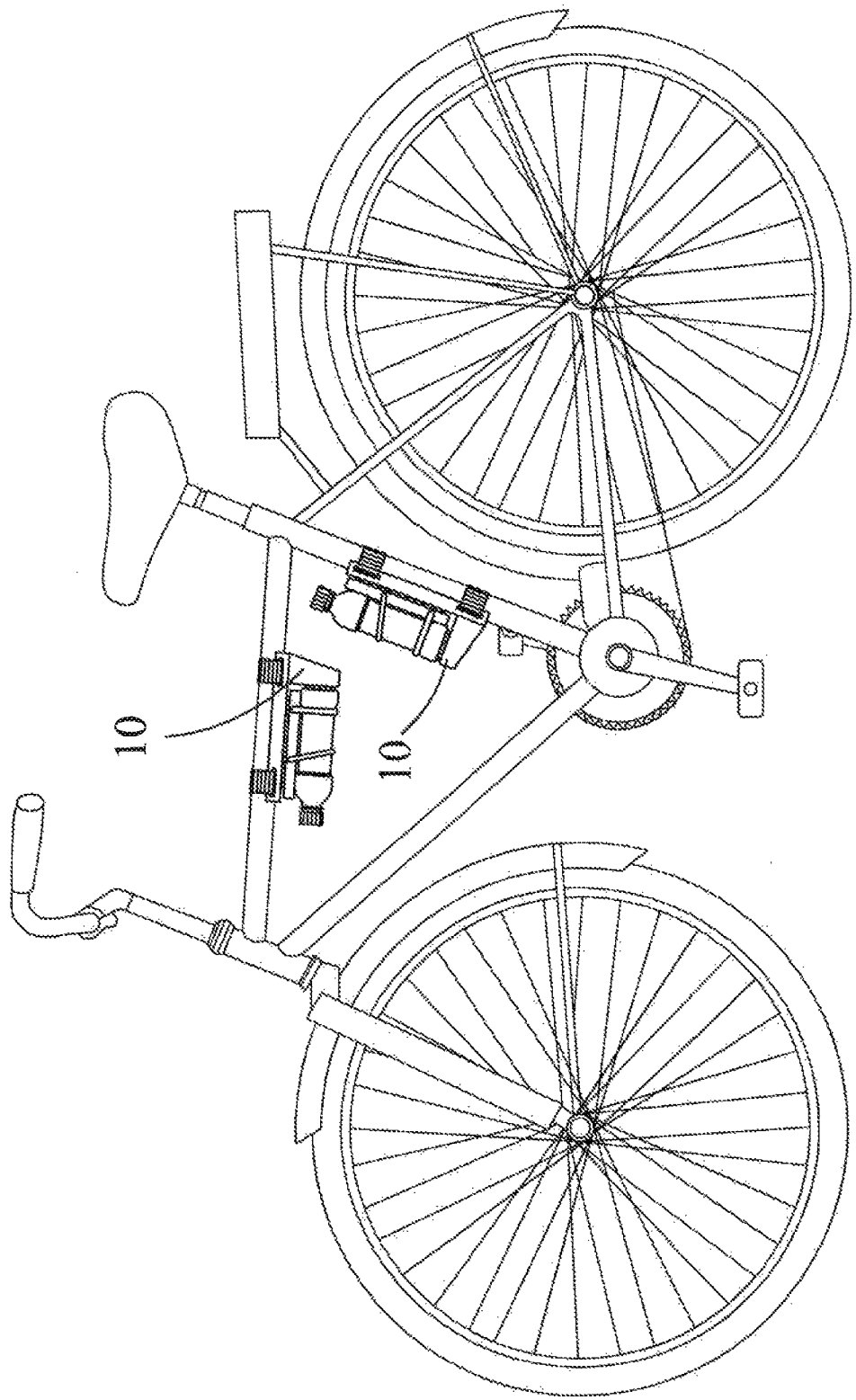
FIG. 6 is a second schematic view of a drinking water reminding system and the reminding method thereof in accordance with the second preferred embodiment of the present invention.

With reference to FIGS. 5 and 6 for the first and second schematic views of a drinking water reminding system in accordance with the second preferred embodiment of the present invention respectively, the reminder 10 is installed on bicycles, steppers or similar fitness equipments. In other words, a fixing element 510 can be used to fix the reminder 10 onto sports equipment, and then the user can place a container 520 on the reminder 10 and use a fixture 500 to fix the reminder 10. Wherein, a load cell sensor 160 can be of a compressive form or a telescopic form, and both can be installed at a position corresponding to the desired position of setting the reminder 10. In FIG. 6, if the reminder 10 is installed upside down and onto the fitness equipment, then the telescopic load cell sensor 160 can be installed between the container 520 and the fixing element 510. It is noteworthy that the reminder 10 of this preferred embodiment allows users to remember supplementing water anytime during their exercise, so as to prevent uncomfortable symptoms caused by the deficiency of water.

Figure 7:
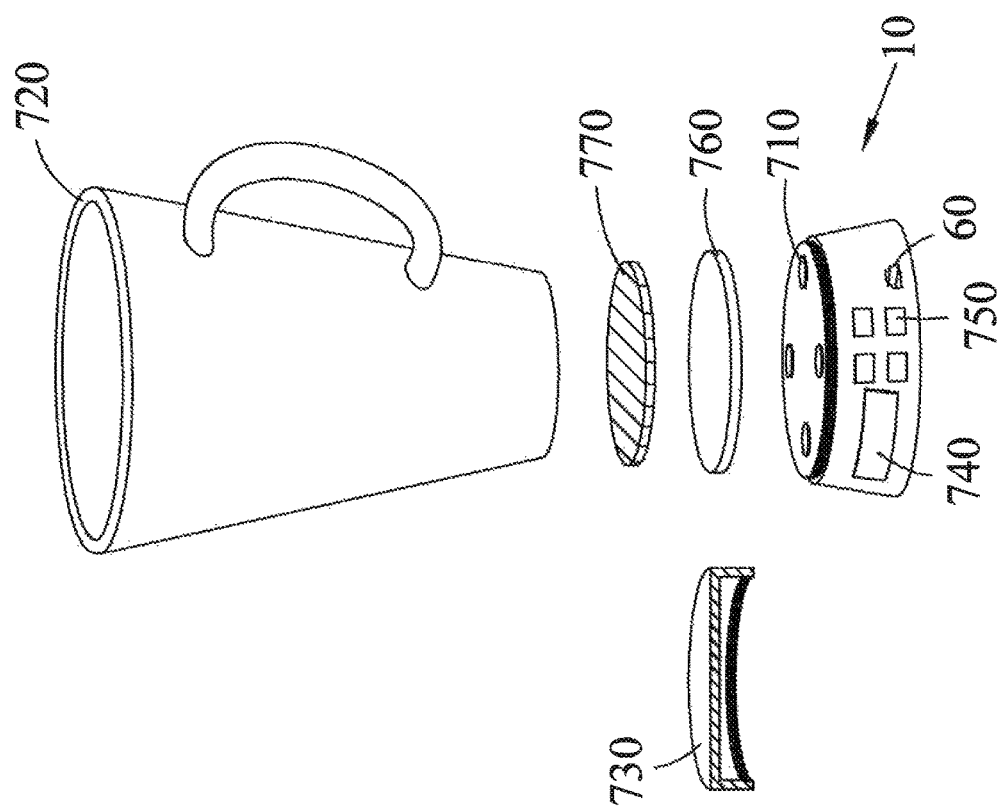
FIG. 7 is a schematic view of a drinking water reminding system and the reminding method thereof in accordance with a third preferred embodiment of the present invention.

With reference to FIG. 7 for a drinking water reminding system in accordance with the third preferred embodiment of the present invention, the reminder 10 can be installed according to the shape and dimensions of the container 720 or the user's personal preference. Wherein, the reminder 10 of this preferred embodiment can use an attaching component 710 corresponding to an attaching pad 760 and an attaching layer 770 for mounting various different containers 720. For example, the attaching component 710 includes but not limited to a magnet, a Velcros tape, a latching element or a locking element. The attaching pad can be made of metal, plastic or ceramic. The attaching layer can be an adhesive layer with a frictional layered structure. It is noteworthy that a fastener 730 can be used to connect the reminder 10 by using screw threads or serration to provide diversified applications of the reminder 10, and the functions of the touch screen 740, the press button 750 and the interface conversion device 60 installed on the reminder 10 has been described in the foregoing preferred embodiments and thus will not be repeated.

With reference to FIG. 8 for a schematic view of a drinking water reminding system in accordance with the fourth preferred embodiment of the present invention, the drinking water reminding system 1, the reminder 10 of this preferred embodiment is integrally formed with the container 820 to facilitate the user to carry and keep records and reminders, and also prevent the user from forgetting to put the cup back onto the reminder 10, which may result in an inaccurate record. Wherein, the load cell sensor 160 can be a compressive sensor or a telescopic sensor, and the two can be operated together with the reminder 10 and installed at a position where the container 820 is integrally formed. In this preferred embodiment, the integrally formed reminder 10 further includes a plurality of magnets 810 for attracting and fixing the metal fixing element 840. In other words, different fixing angles are provided, so that the reminder 10 can measure the content in the container 820 from different angles of placing the load cell sensor 160, so as to calculate the user's required water intake accurately. On the other hand, the integrally formed reminder 10 can include an interface conversion device 60 connected to various electronic devices for transmitting the measurement result and the reminding action.

Figure 9:
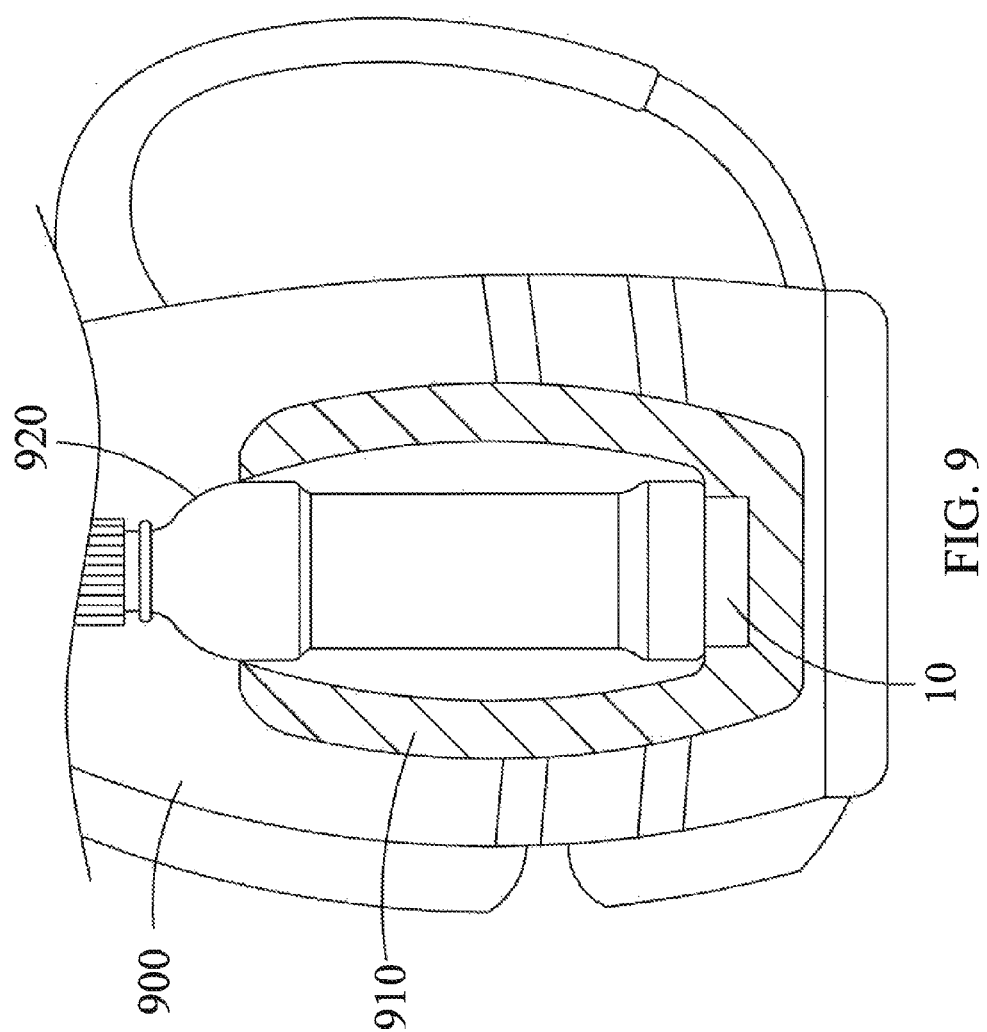
FIG. 9 is a schematic view of a drinking water reminding system and the reminding method thereof in accordance with a fifth preferred embodiment of the present invention.

With reference to FIG. 9 for a schematic view of a drinking water reminding system in accordance with the fifth preferred embodiment of the present invention, the reminder 10 of the present invention is applied to a container 900 including but not limited to various different backpacks. The user can use the reminder 10 of the present invention and an appropriate fastener 910 to contain the fastener 910 in the container 920, and the reminder 10 of this preferred embodiment cam achieve the effect of reminding the user to drink water.

Figure 10:
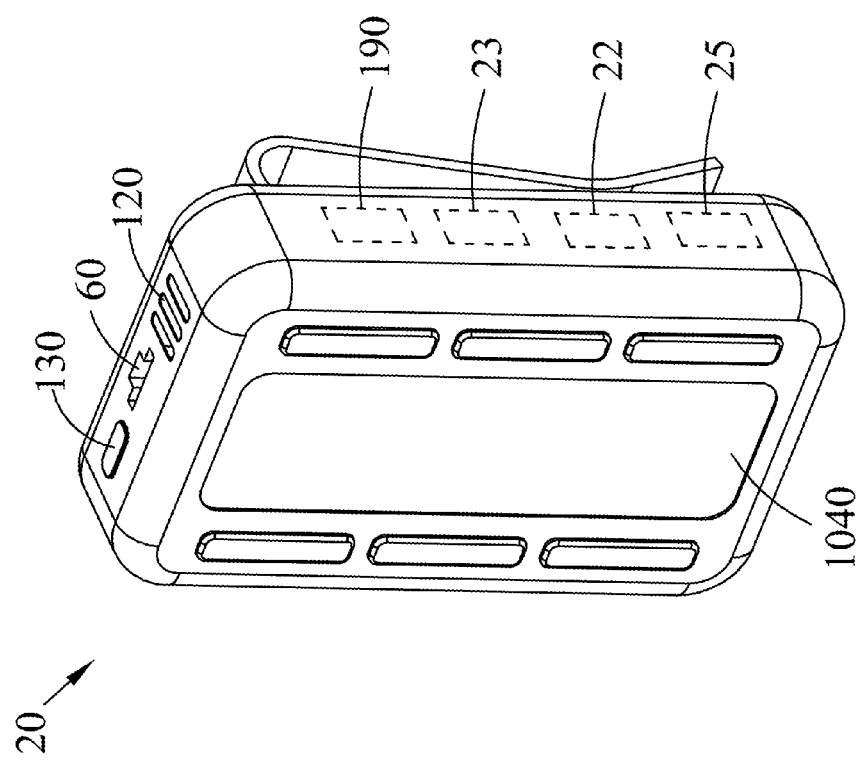
FIG. 10 is a first schematic view of a drinking water reminding system and the reminding method thereof in accordance with a sixth preferred embodiment of the present invention.
Figure 11:
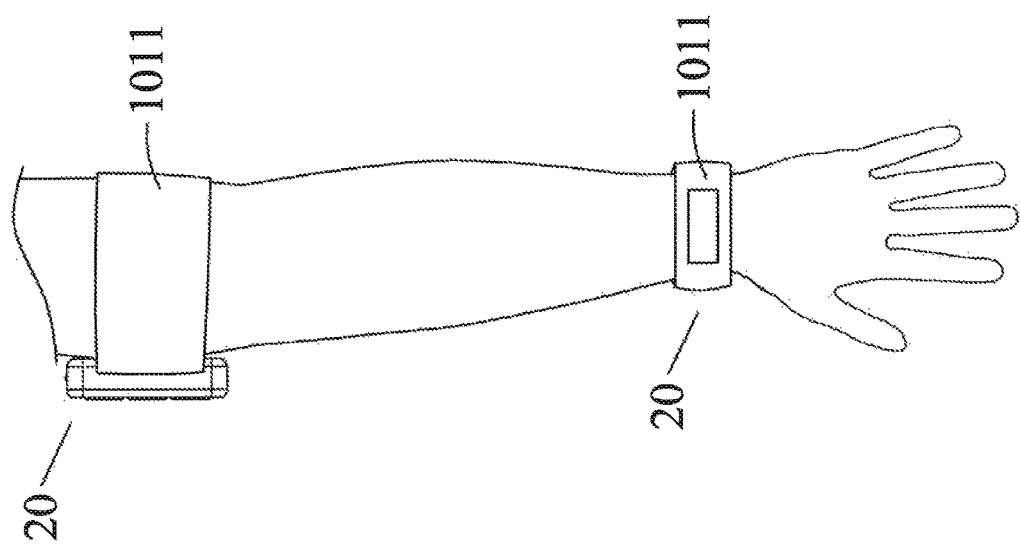
FIG. 11 is a second schematic view of a drinking water reminding system and the reminding method thereof in accordance with the sixth preferred embodiment of the present invention.
Figure 12:
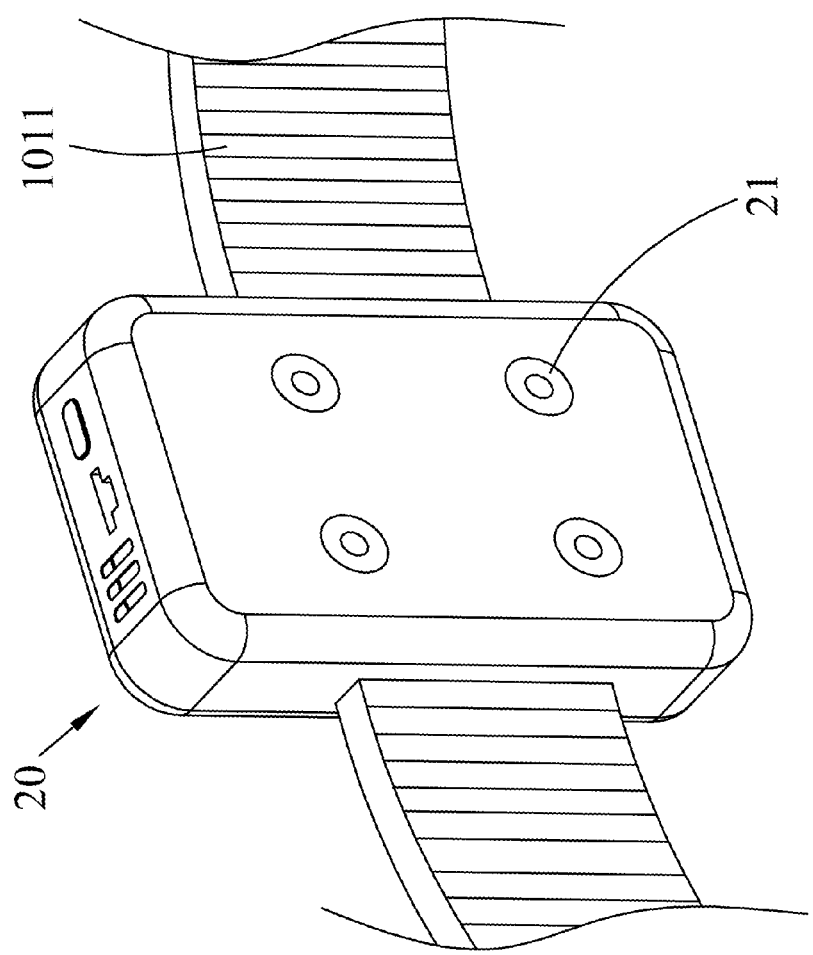
FIG. 12 is a third schematic view of a drinking water reminding system and the reminding method thereof in accordance with the sixth preferred embodiment of the present invention.

With reference to FIGS. 10 to 12 for the first, second and third schematic views of a drinking water reminding system in accordance with the sixth preferred embodiment of the present invention respectively, a touch screen 1040, a control circuit, a battery, a second transmission module 25 such as a radio frequency (RF), infrared or Bluetooth transmission module, a second processing module 22, a second storage module 23, a second reminding module 24 such as an LED 130, a vibrating motor 190, or a buzzer 120 can be built in the collector 20 of this preferred embodiment for reminding the user to drink or supplement water even through the vibration, sound or light of the collector 20 when the user is situated at a position away from the reminder 10 or a noisy place or doing exercise.

Since the time available for the user to supplement water (except the sleeping time) is up to 10~18 hours, therefore one or more reminders 10 may be used in office or at home. As long as the user connects one or more reminder 10 online and wears a paired collector 20, the data collector 20 can transfer a previous record to the next reminder 10 and continue reminding the user to take the remaining required water intake. For example, when the user is off from work and leaves the reminder 10 in the office, the collector 20 transmits the measurement results, the measurement signals, and the predetermined conditions stored in the first storage module 13 before leaving the office to the other reminder(s) 10 at home on the way of driving home or going home, so that the second reminder (s) 10 can continue the incomplete reminding and recording work, until the reminders 10 are returned to the valid range of the connection and pairing. Therefore, the complete measurement result, measurement signal, and predetermined condition can be uploaded and saved into the server 30.

It is noteworthy that the collector 20 of this preferred embodiment of the present invention can be fixed to the user's body such as the user's arm by using a fastener 1011 (as shown in FIG. 11) to facilitate the user to carry the collector 20 while the user is doing exercise, prevent the collector 20 from being lost or missed during the exercise, avoid inconvenient storage, and achieve the effect of reminding the user to drink enough water. In addition, the sensing module 21 of the collector 20 of the present invention includes a multi-axis acceleration sensor, an electronic compass or a hygrometer for sensing physiological parameters such as the user's pulse, body temperature and sweat salinity and environmental parameters such as the user's moving speed, acceleration and direction. The collector 20 connected with network can be used to obtain the temperature, humidity and ultraviolet intensity of the location where the user is situated. In other words, the collector 20 can detect the user's exercise, physiological and environmental changes, the user's moving speed, heartbeat, or body temperature anytime. If the aforementioned numeric values or statistical data of the user start rising or dropping significantly, the second processing module 22 will adjust the proportion of the predetermined conditions automatically according to these numeric values, such as increasing or decreasing the user's required water intake, and timely provide the most accurate drinking water reminding action according to the different predetermined conditions. In addition, the aforementioned functions can be installed to an application program of the user's smart handheld device to replace the collector 20 to achieve the same effect.

When the reminder 10 and the collector 20 of the present invention are connected and paired with the server 30, and the collected information are stored in the server 30, different users can log on the server 30 through registration, and inquire the personal drinking water record and the personal drinking water reference table. The users also can browse and reference actual statistical data such as the districts, weather, ethnic origin, age, body weight, sex and type of work provided by users at different places to obtain average data provided by users of different backgrounds, and these data can be used as a reference value for setting the user's personal daily required water intake. The reminder 10 and the collector 20 can adjust the predetermined conditions according to these reference values.

Figure 13:
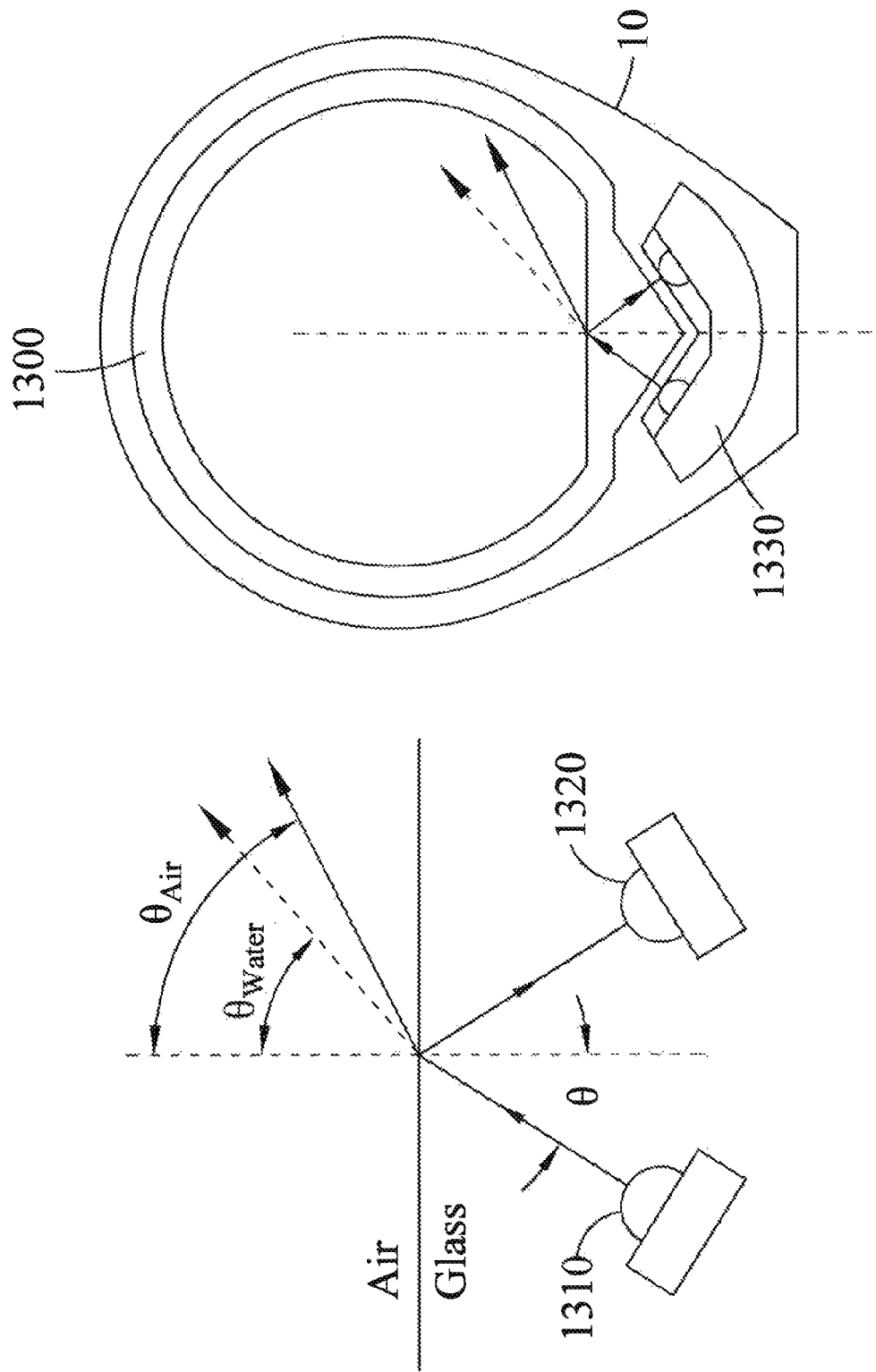
FIG. 13 is a first schematic view of a drinking water reminding system and the reminding method thereof in accordance with a seventh preferred embodiment of the present invention.
Figure 14:
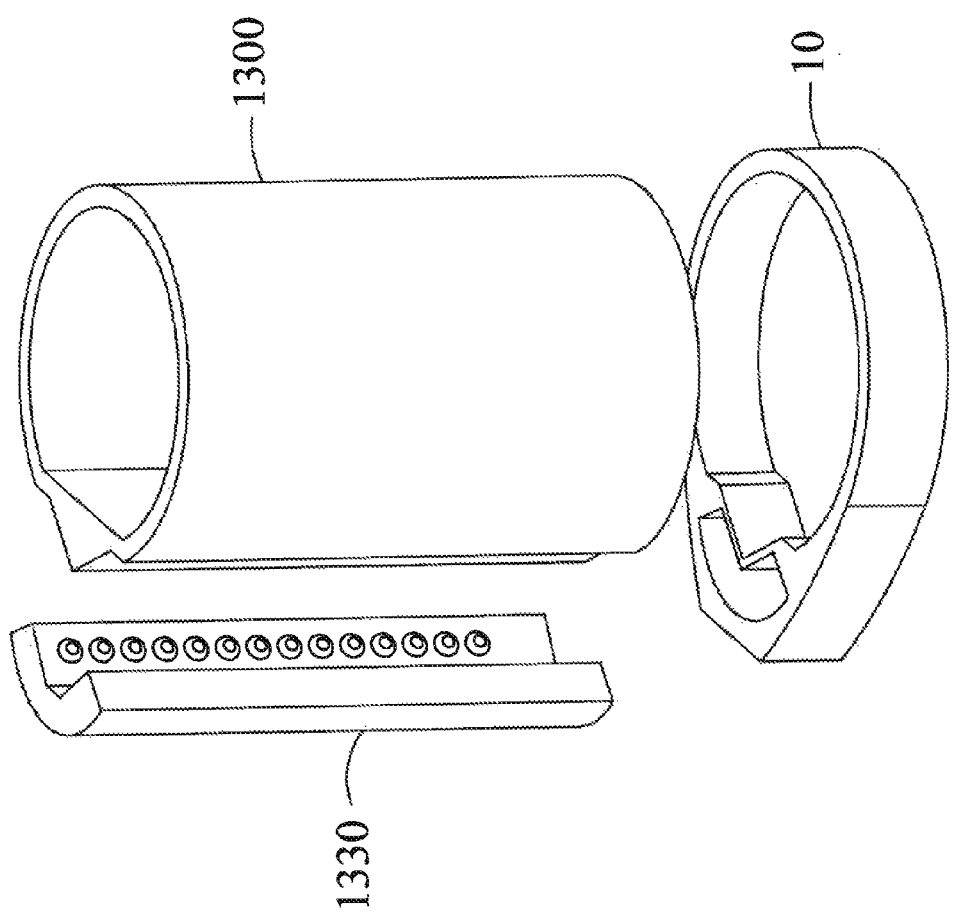
FIG. 14 is a second schematic view of a drinking water reminding system and the reminding method thereof in accordance with the seventh preferred embodiment of the present invention.

With reference to FIGS. 13 to 14 for the first and second schematic views of a drinking water reminding system in accordance with the sixth preferred embodiment of the present invention respectively, the measuring module 11 of the reminder 10 in accordance with this preferred embodiment of the present invention adopts the optical measurement method, wherein an optical transmitter 1310 and an optical receiver 1320 of the optical measuring module 1330 can be used for a light reflection and refraction analysis of the transparent container 1300, and the refractive angles ($\theta_{water}$ and $\theta_{air}$) of the lights (infrared lights) in different media (solution, air or glass) are different, and the signal intensity received by the optical receiver 1320 is also different. Therefore, the height of the solution in the transparent container 1300 can be determined, and the known bottom area of the transparent container 1300 can be used to calculate the consumption of the solution in the transparent container 1300, so as to obtain the measurement signal. Preferably, the optical measuring module includes a plurality of optical transmitters 1310 and optical receivers 1320 installed at positions corresponding to the height of the transparent container 1300 in order to obtain a more accurate measurement signal.

Figure 15:
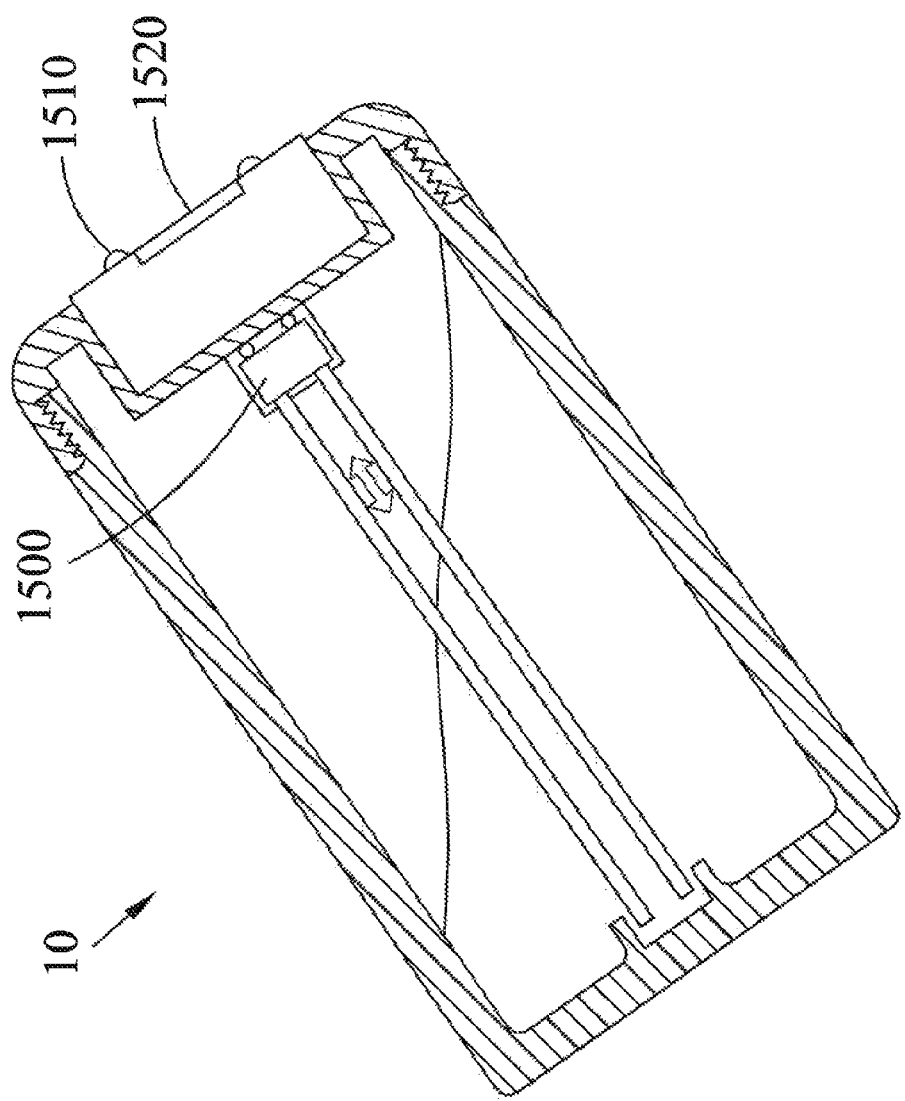
FIG. 15 is a schematic view of a drinking water reminding system and the reminding method thereof in accordance with an eighth preferred embodiment of the present invention.

With reference to FIG. 15 for a schematic view of a drinking water reminding system in accordance with the eighth preferred embodiment of the present invention, the measuring module 11 of the reminder 10 of this preferred embodiment can adopt the ultrasonic measurement method, wherein the ultrasonic measurement module 1500 is a measurement device provided for detecting a change of the water level at a center duct of the container to calculate the water level and quantity, and a press button 1510 is provided for switching on or off the ultrasonic measurement module 1500, and a touch panel 1520 is provided for displaying the reminding action to notice the user. Since the ultrasonic measurement method of this preferred embodiment determines the change of water level at the center duct, this preferred embodiment can calculate the capacity of the content (or water) in the container, when the container is tilted.

Figure 16:
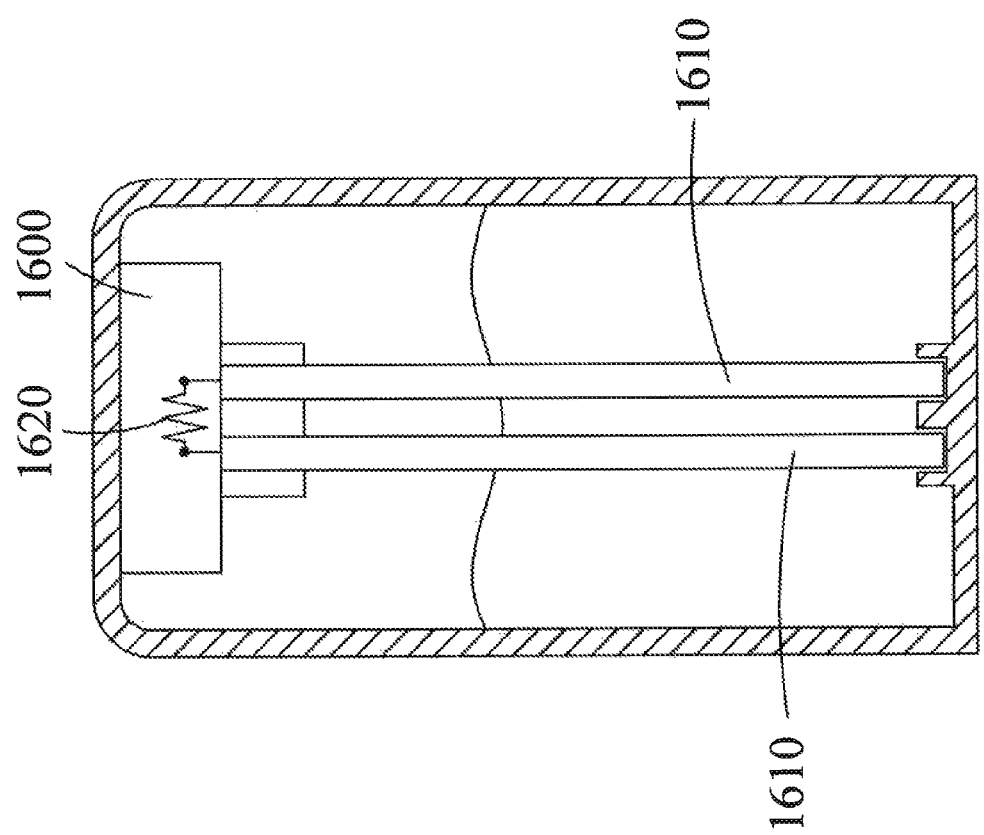
FIG. 16 is a first schematic view of a drinking water reminding system and the reminding method thereof in accordance with a ninth preferred embodiment of the present invention.
Figure 17:
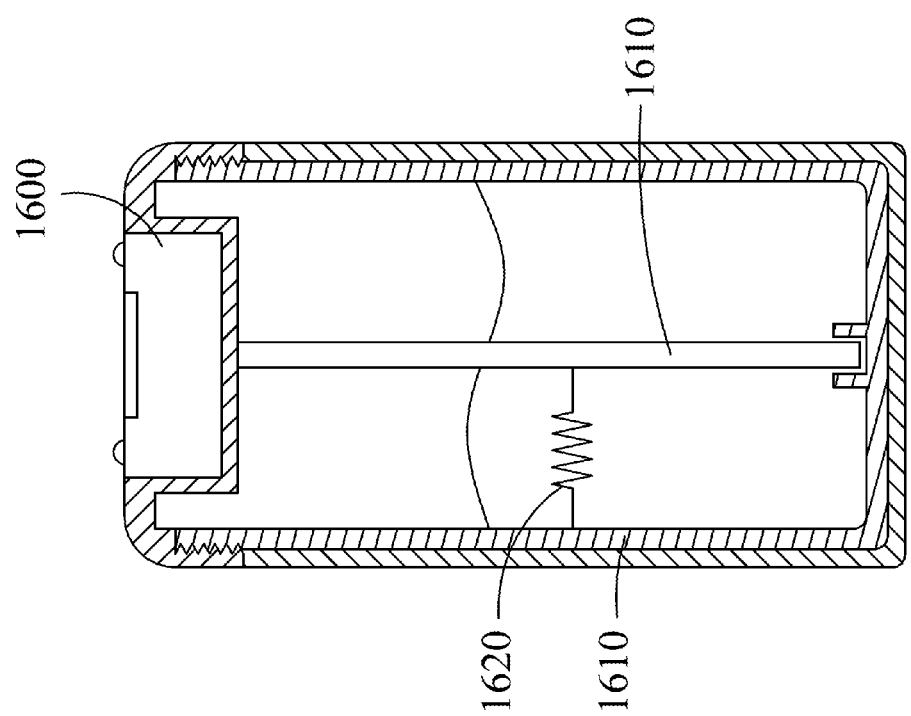
FIG. 17 is a second schematic view of a thinking water reminding system and the reminding method thereof in accordance with the ninth preferred embodiment of the present invention.

With reference to FIGS. 16 to 17 for the first and second schematic views of a drinking water reminding system in accordance with the ninth preferred embodiment of the present invention respectively, an electrical impedance measuring module 1600 is provided for carrying out an electrical impedance variation measurement method and the electrical impedance measuring module 1600 comprises a resistor 1620 and two electrodes (anode and cathode) 1610. The change of the electrical impedance value between the two electrodes 1610 can be used to obtain a change of the liquid level of the content in the container and a change of the content, so as to determine whether or not the user needs to supplement water according to the drinking water program.

While the invention has been described by means of specific embodiments, numerous modifications and variations could be made thereto by those skilled in the art without departing from the scope and spirit of the invention set forth in the claims.

What is claimed is:

1. A drinking water reminding system, comprising:
at least one reminder and at least one collector, each reminder comprising:
a measuring module, arranged for measuring a content in a container to obtain at least one measurement signal by using at least one measurement method;
a first processing module, arranged for receiving the measurement signal and calculating the measurement signal to obtain at least one measurement result;

a first storage module, arranged for storing the measurement result and at least one predetermined condition;

a first reminding module, arranged for performing at least one reminding action according to the predetermined condition and the measurement result; and a first transmission module, arranged for transmitting the measurement signal through a wireless transmission, and each collector comprising:

at least one sensing module, arranged for sensing at least one environmental parameter and at least one physiological parameter;

a second processing module, arranged for receiving the measurement signal and calculating the measurement signal to obtain the measurement result, and further adjusting the predetermined condition according to the environmental parameter and the physiological parameter;

a second storage module, arranged for storing the measurement result and the predetermined condition;

a second reminding module, arranged for performing the reminding action according to the predetermined condition and the measurement result; and a second transmission module, arranged for transmitting the measurement signal and the predetermined condition between the reminder and the collector via the wireless transmission mode;

wherein the collector is a single portable device having the at least one sensing module, the second processing module, the second storage module, the second reminding module, and the second transmission module integrated therein, the collector being separated from the reminder and the container, and when the reminder or the collector establishes a connection and a pairing with each other, the reminder, the collector or combination thereof performs the reminding action, wherein when the reminder and collector designed to be paired are unable to connect with each other, the first reminding module and the second reminding module perform the reminding action according to the predetermined condition and the measurement results stored in the first storage module and the second storage module respectively, and until the reminder and collector are reconnected, the measurement result and the predetermined condition stored in the first storage module and the second storage module respectively before the reconnection are synchronously updated and integrated.

2. The drinking water reminding system of claim 1, further comprising:

a server, arranged for synchronously upload and download the measurement result and the predetermined condition to create a personal drinking water record after the reminder or the collector is connected to the server, and creating a personal drinking water reference table according to a plurality of user data;

wherein, the server stores the measurement result, the predetermined condition or the personal drinking water reference table of different users in order to provide the reference of daily water drinking adjustment to different users.

3. The drinking water reminding system of claim 2, wherein the reminder and the collector further include an interface conversion device connected to at least one electronic device via a cable or wireless connection for transmitting the reminding action, the personal drinking water record or the personal drinking water reference table to the electronic device and notifying an application program of the at least one electronic device of other persons to assist monitoring and reminding the user through a network software application or the wireless connection signal while performing the reminding action.

4. The drinking water reminding system of claim 1, wherein when the reminder and collector designed to be paired are unable to connect with each other, the collector issues an offline warning to notice the user that the reminder and the collector are unable to be connected, and the collector further provides an user input interface for the user to input the amount of water intake of the user during the period when the reminder and the collector are unable to establish the connection, and when any one of the reminder and the collector are reconnected and paired, the measurement signal, the measurement result and the amount of water intake are synchronously updated to the reminder and the collector.

5. The drinking water reminding system of claim 1, wherein the at least one measurement method includes a weight measurement method, an optical measurement method, an ultrasonic measurement method or an electrical impedance variation measurement method.

6. The drinking water reminding system of claim 1, wherein the first reminding module and the second reminding module include a light emitting unit, a sound unit, a vibrating unit or combination thereof.

7. The drinking water reminding system of claim 1, wherein the at least one predetermined condition includes a change of weight within a predetermined time or a drinking water weight set by the user.

8. The drinking water reminding system of claim 1, wherein the sensing module includes a global positioning system, a multi-axis accelerometer, an electronic compass, a gyroscope, a hygrometer or a physiological signal sensor.

9. The drinking water reminding system of claim 1, wherein the environmental parameter includes temperature, humidity and ultraviolet levels of the location of user and the moving speed, acceleration or direction of the user.

10. The drinking water reminding system of claim 1, wherein the physiological parameter includes pulse, body temperature or sweat salinity of the user.

11. The drinking water reminding system of claim 1, wherein the reminder is connected to the container by an attaching component corresponding to an attaching pad and an attaching layer;

wherein the attaching component comprises a magnet, a Velcro's tape, a latching element or a locking element, and the attaching pad is made of metal, plastic or ceramic, and the attaching layer is an adhesive layer with a frictional layered structure.

12. The drinking water reminding system of claim 1, wherein the reminder is connected to the container by a fastener having screw threads or serration.

13. An operation method of a drinking water reminding system, wherein the drinking water reminding system comprises the structure of claim 1, and the method comprising the steps of:

performing the measurement method by the measuring module of the reminder to obtain the measurement signal;

sensing the environmental parameter and the physiological parameter by the sensing module of the collector;

establishing a connection between the first transmission module of the reminder and the second transmission module of the collector through the wireless transmission to transmit the measurement signal, the environmental parameter, the physiological parameter, the predetermined condition or combination thereof;

calculating the measurement signal to obtain the measurement result by the first processing module or the second processing module and adjusting the predetermined condition according to the environmental parameter and the physiological parameter, and storing the measurement result and the predetermined condition in the first storage module and the second storage module; and performing the reminding action according to the predetermined condition and the measurement result by the first reminding module, the second reminding module or combination thereof.

14. The method of claim 13, further comprising the steps of:

performing the reminding action by the first reminding module and the second reminding module according to the predetermined condition and the measurement results stored in the first storage module and the second storage module respectively when the reminder and collector designed to be paired are unable to connect with each other; and synchronously updating and integrating the measurement result and the predetermined condition stored in the first storage module and the second storage module respectively before the reconnection when the reminder and collector are reconnected.

15. The method of claim 14, further comprising the step of:

issuing an offline warning by the collector to notice the user that the reminder and the collector designed to be paired are unable to connect with each other when the reminder and the collector are unable to establish the connection;

providing a user input interface for the user to input the amount of water intake of the user during the period when the reminder and the collector are unable to establish the connection.

16. The method of claim 15, further comprising the step of:

synchronously updating the measurement signal, the measurement result and the amount of water intake in the reminder and the collector, when any one of the reminder and the collector reconnected and paired.

17. The method of claim 13, further comprising the steps of:

synchronously receiving the measurement result and the predetermined condition to create a personal drinking water record and using a plurality of user data to create a personal drinking water reference table by the server after the reminder or the collector has been connected the server;

wherein the server stores the measurement result, the predetermined condition or the personal drinking water reference table of different users in order to provide the reference of daily water drinking adjustment to different users.

18. The method of claim 17, wherein the reminder and the collector further include an interface conversion device connected to at least one electronic device via a cable or wireless connection for transmitting the reminding action, the personal drinking water record or the personal drinking water reference table to the electronic device.

19. The method of claim 17, wherein when the reminder or the collector is connected to the server or electronic device being connected to the server, the environmental parameter or the physiological parameter is uploaded into the server for personal record, and the server further download user location weather forecast parameter or meteorological parameter to the reminder or the collector, so the personal drinking water reference table stored in the reminder or the collector could be updated immediately by the environmental parameter, the physiological parameter, the weather forecast parameter and the meteorological parameters.

20. The method of claim 13, wherein the measurement method includes a weight measurement method, an optical measurement method, an ultrasonic measurement method or an electrical impedance variation measurement method.

21. The method of claim 13, wherein the first reminding module and the second reminding module include a light emitting unit, a sound unit, a vibrating unit or combination thereof.

22. The method of claim 13, wherein the at least one predetermined condition includes a change of weight within a predetermined time or a drinking water weight set by the user.

23. The method of claim 13, wherein the sensing module includes a global positioning system, a multi-axis accelerometer, an electronic compass, a gyroscope, a hygrometer or a physiological signal sensor.

24. The method of claim 13, wherein the environmental parameter includes temperature, humidity and ultraviolet levels of the location of user and the moving speed, acceleration or direction of the user.

25. The method of claim 13, wherein the physiological parameter includes pulse, body temperature or sweat salinity of the user.

* * * * *